United States Patent [19]

Van Brocklin

[11] Patent Number: 4,674,658
[45] Date of Patent: Jun. 23, 1987

[54] FLUID DISPENSER
[75] Inventor: Owen F. Van Brocklin, Bristol, Conn.
[73] Assignee: Risdon Corporation, Naugatuck, Conn.
[21] Appl. No.: 772,563
[22] Filed: Sep. 4, 1985
[51] Int. Cl.⁴ .............................................. B76D 5/52
[52] U.S. Cl. .................................... 222/137; 222/145; 137/576; 141/23
[58] Field of Search ............... 222/145, 135, 137, 136, 222/96, 160, 185, 335, 372, 373, 634, 409, 631; 137/255, 575, 576, 581; 141/105, 21, 25, 23, 26; 251/4, 7, 9; 366/182, 130

[56] References Cited
U.S. PATENT DOCUMENTS

| | | | |
|---|---|---|---|
| 1,977,571 | 10/1934 | Brumm | 137/575 |
| 3,100,102 | 8/1963 | Haan | 251/9 |
| 3,237,808 | 3/1966 | Witt et al. | 222/145 |
| 3,960,174 | 6/1976 | Latimer et al. | 137/575 |
| 4,429,852 | 2/1984 | Tersteegen et al. | 251/9 |

Primary Examiner—Joseph J. Rolla
Assistant Examiner—Kenneth Noland
Attorney, Agent, or Firm—St. Onge, Steward, Johnston & Reems

[57] ABSTRACT

A device for mixing and dispensing fluid is disclosed and comprises first and second containers each having a valve for dispensing fluid. The valve is normally biased to a closed position and operable against said bias to an open position. Piston and cylinder elements define a chamber for receiving the fluids. The piston element is movable in response to dispensing of fluid into said chamber. The piston element is operably connected to the valves and exerts a force on the valves to maintain them in an open position. The mixed fluids in the chamber are thereafter dispensed through a handpiece.

22 Claims, 13 Drawing Figures

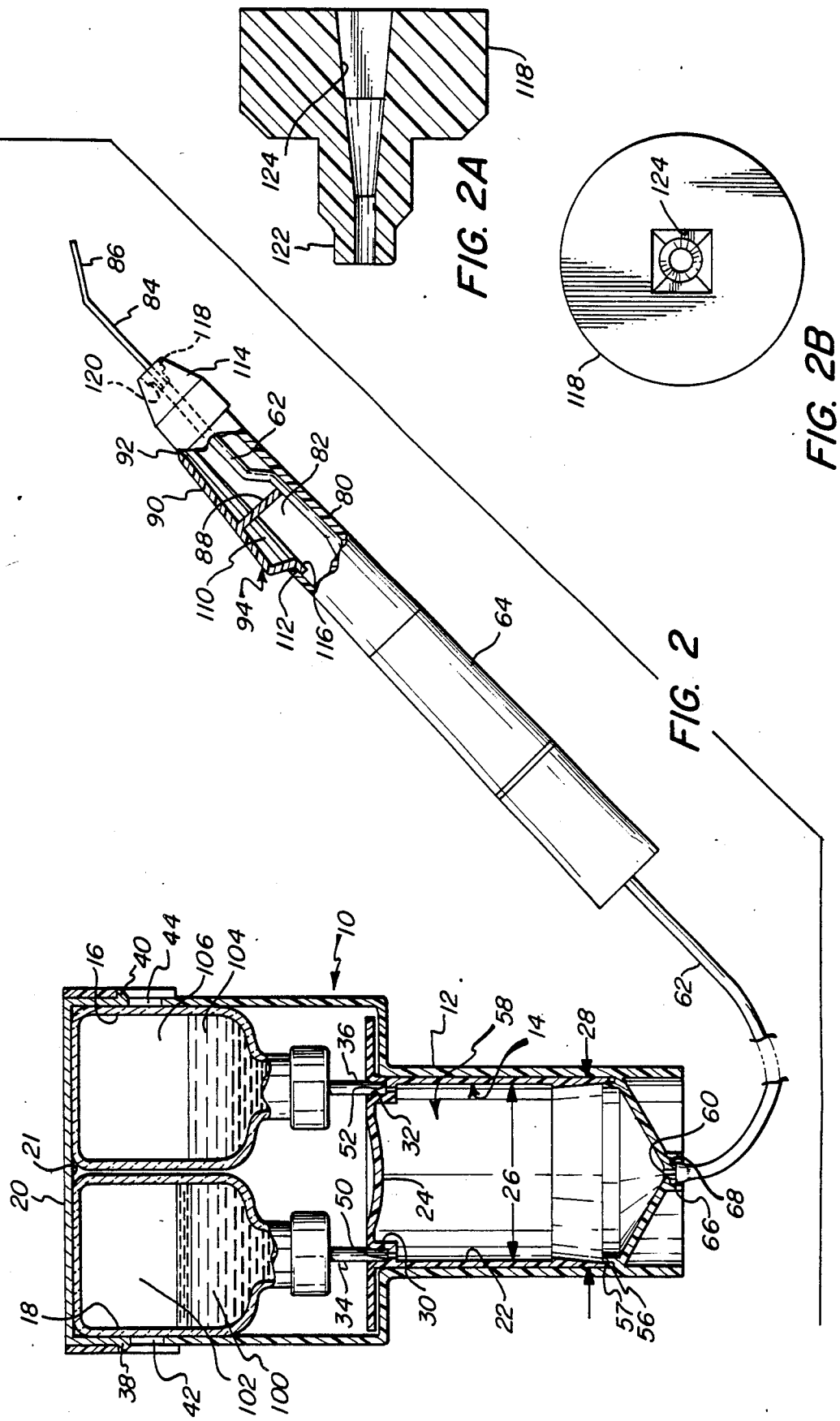

FLUID DISPENSER

BACKGROUND OF THE INVENTION

1. Field of the Invention

The present invention relates to the dispensing of fluids stored under pressure, and, more specifically relates to an apparatus and method for dispensing of two fluids, mixing the two fluids and applying the mixture. Additionally, the present invention relates to a mechanism for maintaining a valve of an aerosol container in an open condition once the valve has been initially actuated to provide dispensing of substantially all contents of the container to be dispensed.

2. Description of the Prior Art

It is desirable to dispense fluid from a relatively inexpensive disposable package such as an aerosol container or similar pressurized container. In some applications, it is desirable to dispense fluids from two or more separate containers which contain different fluids. The fluids may be designed to react with each other and/or one fluid may be chemically unstable or uncompatible with one or more of the other chemicals. One use, for example, is in periodontal applications where it is desirable to mix two incompatible chemicals as disclosed in U.S. Pat. No. 4,521,403. One such device for dispensing fluids from a plurality of containers is disclosed in U.S. Pat. No. 3,613,956 to Roger L. McCulloch. The McCulloch patent discloses to two aerosol dispensing containers having hollow valve stems that are displaceable to discharge fluid under pressure from the containers. The mechanism for actuating the valve stems comprises a handle that pulls the valve stems inward toward their respective containers to actuate the valves. The valves are manually pulled inwardly by a trigger which is returned to its original position when it is no longer desired to dispense fluid from the aerosol containers. One of the primary disadvantages of a system that contains aerosol valves that may be repeatedly open and closed is that the fluid in the containers are not completely dispensed in one actuation of the valves. Since the pressures and the flow rates through the valves may differ from container to container depending upon the type of fluid being dispensed, the size of the valves, and the pressure in the container, the materials may be mixed in undesirable proportions. In addition, if the containers have equal pressures, but the flow rate through the respective valves is different, the head pressure in the mixing chamber may rise to a level where it prevents flow from one of the containers. Thus, the liquids will not be mixed in the desired proportions. Thus, it is desirable to provide a dispensing device wherein substantially all the fluid from each container is dispensed when the valves of the containers are actuated, and wherein the valves are locked in an open position. It is also desirable to provide a device and method of operation wherein both containers fully dispense and build up of pressure in the mixing chamber do not present further dispensing from one container.

In instances where a fluid is being dispensed from a single container or a plurality of containers containing fluid under pressure, it is desirable to insure that the substantially all of the fluid is expelled from each container when its respective valve is actuated. Thus, in prior art aerosol dispensing devices, the valve is typically held down either manually or by a mechanical locking means which are actuated once the valve stem is depressed toward the container. For example, U.S. Pat. No. 3,887,112 to Bolduc et al, U.S. Pat. No. 2,936,756 to Gabriel; U.S. Pat. No. 3,191,808 to Spalazzi et al and U.S. Pat. No. 3,245,586 to Haggit disclose mechanisms for maintaining one or more aerosol valves in an open condition.

When the valve is manually maintained in an open position, only one hand of the person using the dispensing device is available to manipulate other things. Thus, it is an object of the invention to provide a dispensing device which maintains the valve in the open position once it is actuated, without the need for the person operating the device to apply pressure to maintain the valve in its open position. It is also an object of the invention to provide a simple mechanism for maintaining one or more container valves in an open condition. Additional objects will be apparent from the description which follows

SUMMARY OF THE INVENTION

In accordance with one aspect of the present invention, a device for mixing and dispensing fluid is provided and comprises at least a first and a second container each having a valve for dispensing the fluid. Each valve is normally biased to a closed position and operable against the bias to an open position. A device also includes a mixing chamber for receiving the fluids from both containers. The device includes a mechansim for actuating both of the valves to dispense fluids into the chamber and such mechanism may include a plunger which pushes the containers downwardly to force the valves to actuate. Once the valves are actuated, fluid under pressure is dispensed into the chamber. A device in accordance with this aspect of the invention includes a mechanism responsive to an increase in pressure in the mixing chamber for simultaneously maintaining both the valves in an open position. In accordance with a preferred embodiment of the invention, piston and cylinder elements define the chamber that receives the fluid. One of the elements is movable in response to an increase in pressure in the chamber and is operably connected to the valves to exert a force on the valve to maintain it in an open position In accordance with a preferred aspect of the invention, the piston element is slidable within the cylinder element and the piston element is movable from a rest position toward the upper portion a case which houses the piston and the chamber. The piston element includes two passages which receive the valves and permit flow through these passageways into the chamber.

In accordance with the above described aspect of this invention, the containers are movable reciprocally with respect to the case from an initial position toward the piston element. When the containers are moved downwardly, the valve stems of the valves are pressed inwardly to open the valves and dispense fluid under pressure into the mixing chamber. When the pressure in the chamber increases, the piston is forced upwardly and maintains the valve in an open position.

Thus, the above described device is advantageous in that the entire contents of the containers is dispensed. Also, after an initial manual operation of the plunger to move the containers downwardly, the valves are maintained in an open position by the piston element which is forced upwardly by the increased pressure in the mixing chamber. Thus, after an initial manual actuation, the valves are maintained in an open position dispensing fluid into the chamber. The dispensing device includes a mechanism for dispensing fluids from the mixing chamber such as a fluid transfer line from the chamber to a handpiece which may be manually controlled to dispense the mixed fluids. Thus, the increased pressure in the head space of the mixing chamber provides the dispensing force for the mixture.

In accordance with another aspect of the invention, the device can include a single container and provides a single shot device for dispensing fluid. Thus, where it is desirable to dispense all of the fluid from a single pressurized container once the container valve is initially actuated, the piston element maintains the valve in an open condition.

In accordance with a preferred aspect of the invention, the device includes a case having an upper portion sized and shaped to store at least one container and has a lower portion forming the cylinder element. By using the case itself to form an integral cylinder element, a multiplicity of parts may be avoided and the device is simplified and consists essentially of a case having an integral cylinder element, a piston element and two valved aeresol containers. Additional features and advantages will be described in the detailed description of the invention which follows.

BRIEF DESCRIPTION OF THE DRAWINGS

FIG. 2 is a sectional view of the device shown in FIG. 1 assembled and prior to actuation;

FIG. 2A is a sectional view of a hub that is inserted into the end cap of the handpiece;

FIG. 2B is side plan view of said hub;

FIG. 6 is a graph showing pressure versus time of the propellant in the head space of the container containing 10 cc of hydrogen peroxide;

FIG. 7 is a graph showing pressure versus time of the propellant in the head space of the container containing 10 cc providone iodine;

FIG. 8 shows the pressure in the chamber over a period of time;

FIG. 9 shows the volume of peroxide in its container over a period of time;

FIG. 10 shows the volume of providone iodine in its container over a period of time; and FIG. 11 shows the volume of the mixture of hydrogen peroxide and providone iodine in the chamber over a period of time.

DETAILED DESCRIPTION OF THE DRAWINGS

Figure 1:
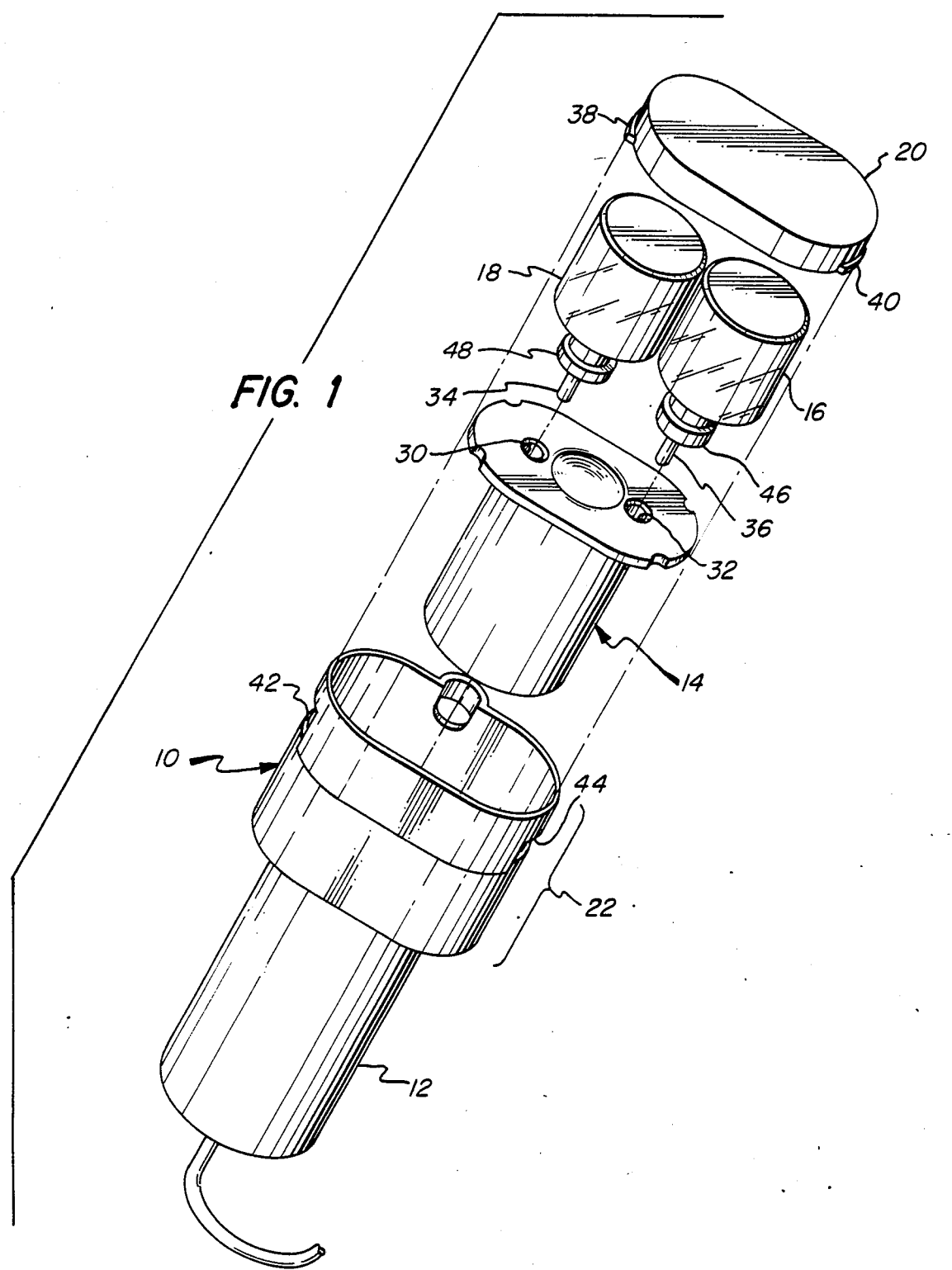
FIG. 1 is an exploded perspective view of a device in accordance with the present invention.
Figure 5:
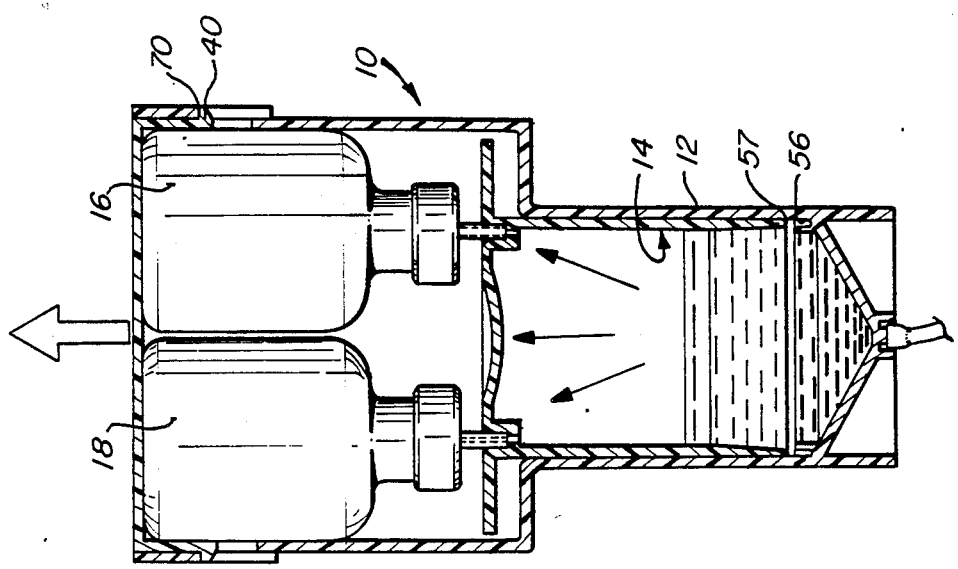
FIG. 5 is a view similar to that shown in FIGS. 2-4 with the exception that the plunger and containers have been returned to their original position and the piston element has risen to maintain the valves of the containers in an open position.

Referring to FIGS. 1 and 2 the various components of the device for mixing and dispensing fluid is shown. The device comprises a casing 10 including an integral cylinder element 12, a piston element 14, two containers 16 and 18 and a plunger 20. The casing has an upper portion 22 sized and shaped to store at least one container. More specifically, the upper portion of the casing is sized to receive the pressurized container or containers in which the fluid to be dispensed is stored. It may be desirable to store and dispense a single fluid, in which case the upper portion 22 would be sized to receive a single container. If multiple containers are desired for dispensing different fluids, the container is shaped to receive such multiple containers. In the case of the device shown in FIG. 1, two containers having a generally cylinderical shape are used. Thus, the cross-section of the upper portion 22 of the casing has the general shape of an oval. The casing has an integral cylinder and element 12 sized and shaped to receive the piston element 14.

Referring in particular to FIG. 2, the piston element 14 comprises a cylindrical sleeve 22 having cap 24 at one end thereof. Cap 24 functions as a piston sliding with respect to cylinder element 12. The cylinder element 12 has an inner diameter 28 which is sized to receive the sleeve 22 of piston element 14 and provide a fluid seal therebetween.

For each valve and associated container, the cap 24 includes a passageway therein for receiving the valve. In the case of the device shown in FIG. 2, the cap 24 includes two passageways 30 and 32 which are designed to receive valve stems 34 and 36 of containers 18 and 16 respectively.

The device includes a plunger 20 that is slidably received within the upper portion 22. The plunger 20 has two protrusions 38 and 40 that slide respectively in guide openings 42 and 44 of the casing 10. The sliding movement of the plunger 20 is limited between the position shown in FIG. 2 and the position shown in FIG. 4.

The containers 16 and 18 are sealed and capable of withstanding substantial internal pressures, and include dispensing valves 46 and 48. Each of the valves 46 and 48 are normally biased to a closed position and operable against the bias to an open position. Preferably, the valves comprise a stem valve. More particularly, valves 46 and 48 include stems 34 and 36 which are biased to the position shown in FIG. 2 and movable inwardly into the container against the bias to the position shown in FIGS. 3 and 4. When the stem is in the extended position shown in FIG. 2, the valves 46 and 48 are closed. When the stem is moved inwardly, fluid is dispensed through the stem. Referring to FIG. 2, the valves stems 34 and 36 are in abutting relationship with the stop surfaces 50 and 52 on passageways 30 and 32.

At the lower end of the mixing chamber, the cylinder wall includes an annular groove 56 for receiving the annular terminal edge 57 of piston sleeve 22. Thus, in its initial position, the bottom edge piston sleeve 22 is locked within the annular groove to keep any gas initially dispensed into the chamber 58 from leaking into the upper portion 22 of the casing. As the chamber 58 begins to fill, the liquid level is maintained above the location of seal formed between the piston sleeve 22 and the cylinder wall.

The bottom of chamber 58 includes an outlet 60 connected to a flexible tube 62 which extends to handpiece 64. The flexible tube is inserted over a nib 65 into an annular receptacle 66 at the bottom of the device and is secured with respect to the casing by a ring 68 which is force fitted into annular receptacle 66. The ring forces the tube 62 radially inwardly against the nib 65.

The operation of the device will be described sequentially with reference to FIGS. 2 through 5. The casing is held in an upright position as shown in FIG. 2 and the handpiece is manually held in a closed position. Alternatively, the handpiece could be held in a closed position by a mechanical fastener of some type and moved to the open postion when it is desired to dispense a mixture of fluids.

Figure 3:
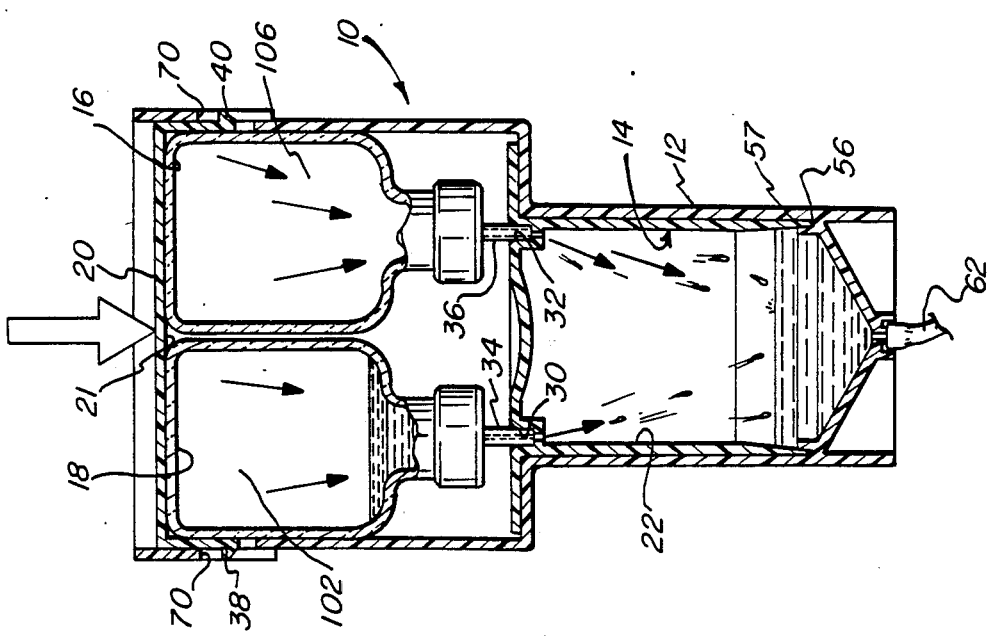
FIG. 3 is a view similar to that shown in FIG. 2 with the exception that the plunger of the device has been depressed to dispense fluid.
Figure 6:
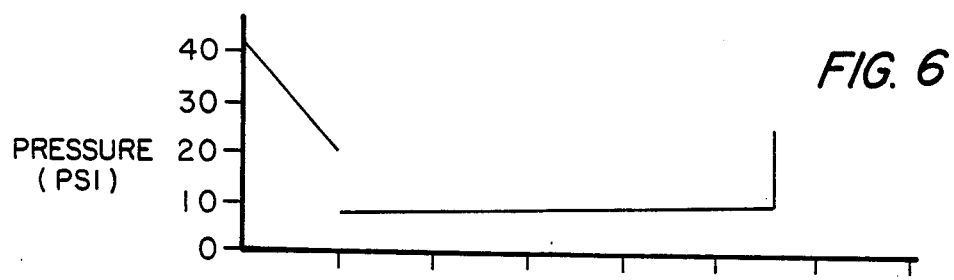
FIGS. 6-11 show graphs depicting various variables during dispensing of fluids from the containers into the mixing chamber and prior to dispensing of the mixture from the mixing chamber.
Figure 7:
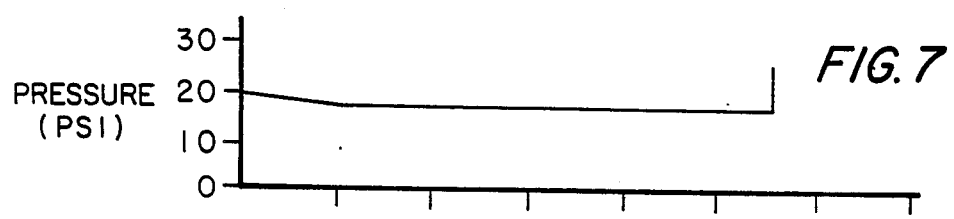
Figure 8:
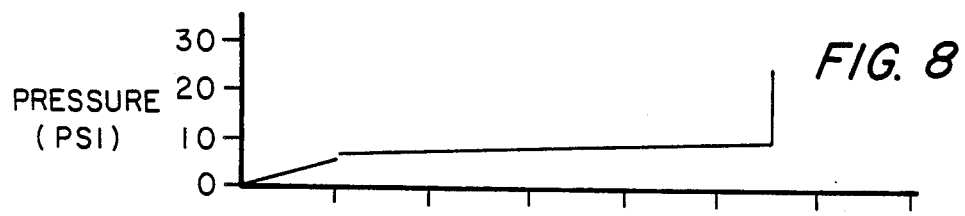
Figure 9:
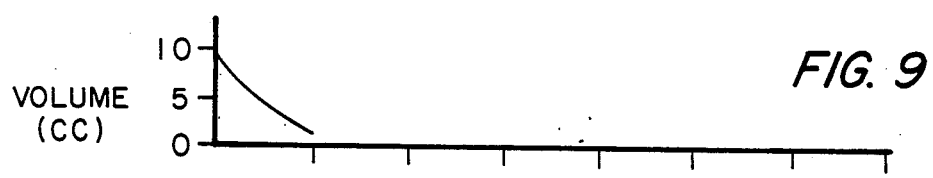
Figure 10:
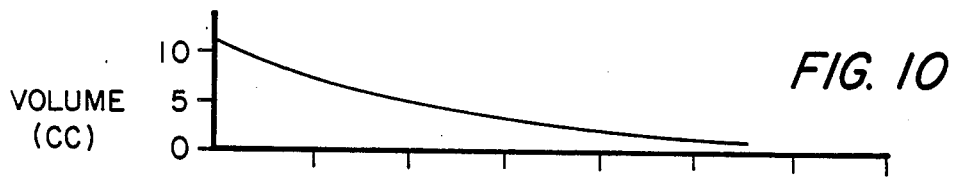
Figure 11:
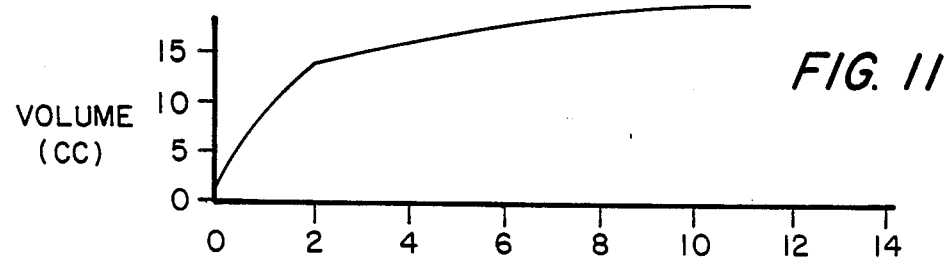

The plunger 20 is pushed downwardly a small distance. Interior face 21 of the plunger contacts the upper surface of the containers and pushes the containers downwardly. A person actuating the device supplies sufficient force to overcome the spring bias on valve stems 36 and 34. As shown in FIG. 3, the containers are pushed downwardly thus actuating the valves to dispense fluid into chamber 58. The plunger as it moves downwardly not only urges the containers downwardly, but also pushes the sleeve 22 downwardly so that the annular groove 56 engages the edge 57 of the sleeve. Thus, gas dispensed into the chamber 58 is prevented from leaking by a positive mechanical and frictional seal.

Figure 4:
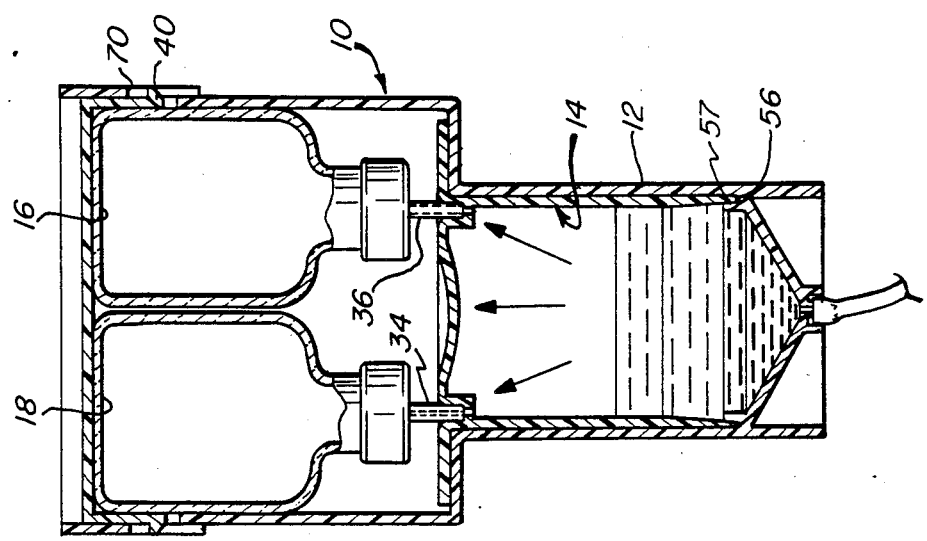
FIG. 4 is a view similar to that shown in FIGS. 3 and 4 with the exception that fluid has been completely dispensed from the containers.

Once sufficient manual force is placed on the plunger, the valves are actuated and dispense the liquid into the chamber as shown in FIG. 4. When the pressure in the chamber 58 increases, the piston element 14 is urged upwardly against the valve stems 34 and 36 holding the valves open. As hand pressure is released from the plunger 20, the plunger moves upwardly under the force of the pressure in chamber 58 and under the spring bias of valve stems 34 and 36. Once the plunger reaches the position shown in FIG. 5, the plunger is prevented from further movement by the abutment of the annular flange 38 with the stop surface 70 on guide grooves 44 and 42. The piston element 14 continues to move upwardly to the position shown in FIG. 5 wherein the pressure in the chamber is sufficient to overcome the valve bias. The valves are maintained in an open position by the force of the piston element.

It should be understood that the containers are designed such that the pressure in the head space of chamber 58 is sufficient to overcome the spring bias of stems 34 and 36. Thus, the diameter of the piston, the pressure in the head space of the piston after the containers have fully dispensed and the spring bias on the valves 32 and 34 are selected so that the force of the pressure on the piston element is sufficient to overcome the bias of the valves.

Once the fluids in the two containers are dispensed into the chamber 58, the entire casing can be gently agitated to insure complete mixture. After the two fluids are fully mixed, a person may dispense the mixture by operating the handpiece 64.

The handpiece will now be described in detail. The handpiece 64 includes a body 80 having a hollow cavity 82. The tube 62 is run through the hollow cavity 82 to a nozzle 84 which has a narrow tip 86 to permit focused dispensing of the fluid mixture. The tubing 62 is preferably made of a resilient material which biases the pinching mechanism 88 to the open position shown in FIG. 2. The pinching mechanism is secured and preferably integrally formed with a lever 90 which is secured at its end 92 to the body 80 of the handpiece. The person actuating the handpiece pushes down on the lever as indicated by arrow 94 thus forcing the pincher 88 to close the resilient tube 62. When finger pressure is released, the resilient nature of the tube forces the pincher 88 upwardly and allows passage of liquid through the tube to the nozzle 84. In accordance with a preferred aspect of the invention, the body 80 includes an elongate slot 110 extending lengthwise of said body. The slot includes a terminal end 112 at the region of the body farthest away from its dispensing end. The handpiece includes an end cap 114 secured to one end of the body 80. More particularly, the end cap 114 has an inner diameter sized to frictionally receive the outer diameter of body 80. Lever 90 is integral with end cap 114 and extends lengthwise of the body and is aligned with slot 110. The lever has an end 116 extending into the cavity 82 and lengthwise past said slot terminal end 116 thereby retaining the lever 90 against movement away from the body when said lever end 116 contacts said slot terminal end 112. It should be understood that the end cap and integral lever 90 are made of a resilient polymeric material and are sized so that the resiliency of the material urges the lever 90 and therefore the lever end 116 into contact with the terminal end of the slot. Thus, the bias of the lever is provided by the materials from which the lever and end cap 114 are made, and a separate spring or other means for biasing the lever 90 is not required. The pinching mechanism 88 which comprises a stud extending inwardly into the cavity, permits the flexible tube 62 to be pinched. It should be understood that the tube is pinched in various degrees so that not only are on and off modes provided, but also the flow rate through the tube can be controlled by finger pressure on the lever. Stud 88 has a length designed to permit the tube 62 to be in a fully opened position when the lever 90 is biased to the position shown in FIG. 2. The stud 88, when the lever is moved downwardly, closes flexible tube 62.

As shown in FIG. 2A and B, the end cap includes a hub 118 inserted into a receptacle 120 of end cap. As shown in FIGS. 2A and B, the hub includes an end portion 122 extending to the cavity and sized to receive the end of flexible tube 62. The hub includes a passage 124 which diverges as it extends outwardly. As best shown in FIG. 2B, the cross-sectional area of the diverging portion of passage 118 has a cross-sectional shape other than circular. More specifically, the diverging portion has a square cross-section. When the nozzle 84, which is a small diameter piece of metal tubing, is inserted into the passage 118, it is secured in the passage by an epoxy filler. Because the cross-sectional area of the passageway is other than circular, the nozzle 84 will not rotate within the passageway 118. More specifically, an epoxy filler tends to adhere extremely well to the metal tubing of the nozzle 84, but will not adhere well to the plastic from which the hub 118 is formed. Thus, but for the irregular shape, the epoxy would tend to break free from the plastic and rotate within the passageway 118. The irregular cross-section and preferably a square cross-section, prevents rotation of the solidified epoxy thus preventing rotation of the nozzle 84.

As shown in the drawings, the dispensing device has two major pieces, the casing and the handpiece. If desired, the handpiece could be made part of the casing to provide essentially a single piece unit.

Referring to FIG. 2, the fluid in each container includes a liquid component 100 and a gaseous propellant component 102. Container 16 has a fluid having a liquid component 104 and a gaseous propellant component 106. By a liquid component, it is meant a liquid, or a liquid containing solid materials capable of flowing. In order to fully dispense the liquids 100 and 104 from their respective containers, the pressure of gases 102 and 106 must be maintained above the pressure in chamber 58 which is initially at atmospheric pressure.

One example of the use of the device in accordance with the present invention is for the mixture of hydrogen peroxide and providone iodine in periodontal applications. In such an instance, the container 16 is filled with 10 cc of providone iodine and has a pressurized nitrogen head space having a pressure of approximately 42 psig. The other container 18 includes a 10 cc volume of hydrogen peroxide having a 1.5 cc layer of butane and having a propellant head space having a pressure of 17 to 20 psig.

In accordance with one aspect of the invention, the valve stems 34 and 36 have different orifice sizes, which, in turn, effect the time it takes for the valve to dispense the fluid. In accordance with the example, the stem 36 has a 0.050 orifice and the stem 34 has a 0.013 orifice.

The charts in FIGS. 6 through 11 show the pressures of the two containers and the chamber 58 over a period of time and the volume of liquid in the two containers and the chamber over a period of time.

Initially, when the plunger is forced downwardly, the providone iodine is dispensed into the chamber in approximately two seconds. The hydrogen peroxide simultaneously with providone iodine empties into the chamber, but this takes approximately 11 seconds. The pressure in the chamber increases by the addition of the peroxide to 8 to 10 psig. When the butane finally enters the chamber, the pressure therein increases to 25 to 30 psig. The pressure in the chamber 58 is sufficient to overcome the bias of valves 34 and 36. More specifically, the pressure in chamber 58 acts on the effective diameter of the piston and the geometry of the device is selected so that the pressure on the piston is sufficient to overcome the forces provided by the spring bias of valves 34 and 36.

A device in accordance with the present invention is particularly suitable for mixing two or more fluids which are desirably stored separately. In one embodiment of the invention, the device provides a single shot application. That is, once the device is initially actuated, full dispensing of all the components in the containers is insured to provide the desired proportional mixture. Moreover, the device is a single shot device that is relatively inexpensive to manufacture and that may be discarded after a single use. While the device is particularly suitable in periodontal applications where it is desirable to mix providone iodine with hydrogen peroxide, it is apparent that the device can be used to mix components for various other applications.

It should be understood that although specific embodiments of the invention have been described herein in detail, such description is for purposes of illustration only and modifications may be made thereto by those skilled in the art within the scope of the invention.

I claim:

1. A device for mixing and dispensing fluid comprising:
    a first container having valve means for dispensing fluid, said valve means normally biased to a closed position and operable against said bias to an open position;
    a second container having valve means for dispensing fluid, said valve means being normally biased to a closed position and operable against said bias to an open position;
    a chamber for receiving said fluids from both said containers;
    means for actuating both said valve means to dispense said fluids into said chamber; and
    means responsive to an increase in pressure in said chamber for simultaneously maintaining both said valve means in said open position; and
    means for dispensing said fluids from said chamber.

2. A single-shot device for dispensing fluid comprising:
    at least one container storing said fluid under pressure;
    a valve for dispensing said fluid from said container, said valve biased to a closed position and movable by a predetermined force against said biased to an open position;
    means for opening said valve;
    piston and cylinder elements defining a chamber for receiving said fluid, one said element being movable in response to dispensing of fluid into said chamber, said one element being operably connected to said valve and exerting said predetermined force on said valve to maintain it in said open position; and
    means for dispensing fluid from said chamber.

3. A dispenser according to claim 2 and further including a case having upper and lower portions integrally formed in a single piece said lower portion defining said cylinder element, said upper portion storing said at least one container.

4. A dispenser according to claim 3 wherein said valve includes a valve stem movable relative to said container to actuate said valve, said passageway in said piston element being sized and shaped to receive an end portion of said valve stem.

5. A dispenser according to claim 4 wherein said dispenser further includes a plunger for moving said container from said initial position toward said piston, said plunger operable by manual pressure, and slidable reciprocally with respect to the upper portion of the case, said plunger slidable from said initial position to a position wherein said valve is actuated.

6. A dispenser according to claim 5 wherein said cylinder element comprises a cylindrical tube having an inner diameter sized to receive said piston element.

7. A dispenser according to claim 6 wherein said piston element comprises a cylindrical sleeve having a cap at one end thereof, said cap having said passageway therein for receiving said valve, said cap having a sufficient area to overcome said bias of said valve when fluid under pressure is dispensed into said chamber.

8. A dispenser according to claim 7 wherein said sleeve has an annular terminal edge, and wherein said cylinder element includes an annular groove sized to receive and to frictionally engage said terminal edge to form a tight seal between said piston and cylinder elements when they are in an initial position.

9. A dispenser according to 8 wherein said cylinder element has a bottom end portion including a closure defining a sealed chamber, said bottom end portion having an outlet for dispensing fluid from said chamber.

10. A dispenser according to 9 wherein said cylinder includes a stop surface for limiting the downward stroke of the piston.

11. A device for mixing and dispensing fluid comprising:

a first container storing fluid under pressure, said first container having a fixed volume and having valve means for dispensing fluid from said container, said valve means being biased to a normally closed position, and operable against said bias to an open position;

a second container storing fluid under pressure, said second container having a fixed volume and having valve means for dispensing fluid, said valve means being normally biased to a closed position and operable against said bias to an open position;

means for actuating both said valve means to dispense fluid;

chamber connected to said valve means for receiving fluid from both said containers, said chamber having a variable volume, said volume increasing in response to dispensing of fluid within said chamber;

means responsive to said increase in volume for maintaining both said valve means in an open position; and means for dispensing said fluids from said chamber.

12. A dispenser for dispensing fluid under pressure comprising:

at least one container having a fixed volume for storing said fluid under pressure, a valve for dispensing said fluid from said container, said valve being normally biased to a closed position and movable relative to said container against said biased to an open position;

a casing having an upper portion sized and shaped to store at least said one container, said casing having a lower portion forming a cylinder element;

a piston element slidable within said cylinder element, said piston and cylinder elements defining a chamber for receiving said fluid, said piston movable from a rest position toward said upper portion of said case, said piston having a passage permitting flow of fluid from said container to said chamber through said valve;

said container being movable reciprocally with respect to said upper case portion from an initial position toward said piston to move said valve to an open position wherein fluid is dispensed into said chamber; and said piston being forced by pressure in said chamber into engagement with said valve and being movable by said chamber pressure with said container to maintain said valve in an open position.

13. A dispenser according to claim 12 wherein said upper and lower case portions are integrally formed in a single piece.

14. A dispenser according to claim 12 wherein said valve includes a valve stem movable relative to said container to actuate said valve, said passageway in said piston being sized and shaped to receive an end portion of said valve stem.

15. A dispenser according to claim 12 wherein said dispenser further includes a plunger for moving said containers from said initial position toward said piston, said plunger operable by manual pressure, and slidable reciprocally with respect to the upper portion of the case, said plunger slidable from said initial position to a position wherein said valve is actuated, and slidable back to its initial position to prevent further sliding of said containers with respect to said upper portion of said case.

16. A dispenser according to claim 12 wherein said cylinder element comprises a cylindrical tube having an inner diameter sized to receive said piston.

17. A dispenser according to claim 12 wherein said piston comprises a cylindrical sleeve having a cap at one end thereof, said cap having said passageway therein for receiving said valve, said cap having a sufficient area to overcome said bias of said valve when fluid under pressure is dispensed into said chamber.

18. A dispenser according to claim 17 wherein said sleeve has an annular terminal edge, and wherein said cylinder element includes an annular groove sized to receive and to frictionally engage said terminal edge to form a tight seal between said piston and cylinder elements when they are in an initial position.

19. A dispenser according to claim 17 wherein said cylinder has a bottom end portion including a closure defining a sealed chamber, said bottom end portion having an outlet for dispensing fluid from said chamber.

20. A dispenser according to claim 19 wherein said cylinder includes a stop surface for limiting the downward stroke of the piston.

21. A dispenser according to claim 12 and further including a second container having a fixed volume and storing fluid under pressure, said container having a valve normally biased to a closed position and movable relative to said container against said biased to an open position, said piston having a passage for each said valve to permit fluids under pressure to be dispensed and mixed within said chamber.

22. A method for dispensing and mixing at least two fluids stored under pressure in separate containers, said containers having valves biased to a closed position and movable against bias to an open position, said method comprising:

actuating said valves to dispense said fluids into a chamber of piston and cylinder elements;

permitting said chamber to expand and said piston to move with respect to said valves;

forcing said valves into an open position through an operative connection between said piston and said valves under the pressure of fluids in said chamber; and maintaining said valves in an open position by the pressure of fluids in said container.

* * * * *